United States Patent
Felder et al.

(10) Patent No.: US 7,129,195 B2
(45) Date of Patent: Oct. 31, 2006

(54) HETEROGENICALLY CATALYSED GAS-PHASE PARTIAL OXIDATION METHOD FOR PRECURSOR COMPOUNDS OF (METH)ACRYLIC ACID

(75) Inventors: Raimund Felder, Neustadt (DE); Signe Unverricht, Mannheim (DE); Heiko Arnold, Mannheim (DE); Jochen Petzoldt, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 263 days.

(21) Appl. No.: 10/466,244

(22) PCT Filed: Jan. 12, 2002

(86) PCT No.: PCT/EP02/00234

§ 371 (c)(1),
(2), (4) Date: Jul. 15, 2003

(87) PCT Pub. No.: WO02/062737

PCT Pub. Date: Aug. 15, 2002

(65) Prior Publication Data

US 2004/0054222 A1    Mar. 18, 2004

(30) Foreign Application Priority Data

Jan. 15, 2001   (DE) ............................ 101 01 695

(51) Int. Cl.
  *B01J 23/00*    (2006.01)
  *B01J 21/00*    (2006.01)
(52) U.S. Cl. ............ 502/311; 502/248; 502/255; 502/305; 502/312; 502/313; 502/314; 502/316; 502/318; 502/321

(58) Field of Classification Search ............ 502/306, 502/310–314, 316–323, 355, 415, 439, 248, 502/255
See application file for complete search history.

(56) References Cited

U.S. PATENT DOCUMENTS

| | | | | |
|---|---|---|---|---|
| 3,898,267 A | * | 8/1975 | Caporali et al. | 558/322 |
| 3,925,464 A | * | 12/1975 | Oda et al. | 562/535 |
| 4,113,769 A | * | 9/1978 | Padovan et al. | 562/534 |
| 4,166,190 A | * | 8/1979 | White et al. | 562/534 |
| 4,171,454 A | | 10/1979 | Miller et al. | |
| 4,318,738 A | * | 3/1982 | Masumoto et al. | 148/304 |
| 4,321,160 A | * | 3/1982 | Farrington et al. | 502/209 |
| 4,438,217 A | * | 3/1984 | Takata et al. | 502/205 |

(Continued)

FOREIGN PATENT DOCUMENTS

CN    1 105 352    7/1995

(Continued)

OTHER PUBLICATIONS

W. Gerhartz et al.: "Ullmann's Encyclopedia of Industrial Chemistry, vol. A1, Edition 5, (Abrasives to aluminum oxide)" VCH VERLAG, p. 170 1985.

*Primary Examiner*—Cam N. Nguyen
(74) *Attorney, Agent, or Firm*—Oblon, Spivak, McClelland, Maier & Neustadt, P.C.

(57) ABSTRACT

The invention relates to a method for the heterogenically catalyzed gas-phase partial oxidation of precursor compounds of (meth)acrylic acid in a fixed catalyst bed, containing as the catalyst an activated mass of mixed oxide, shaped to form a geometric body. Said geometric body is a geometric base body, into whose surface a cavity is incorporated.

15 Claims, 15 Drawing Sheets

U.S. PATENT DOCUMENTS

Figure 1B:
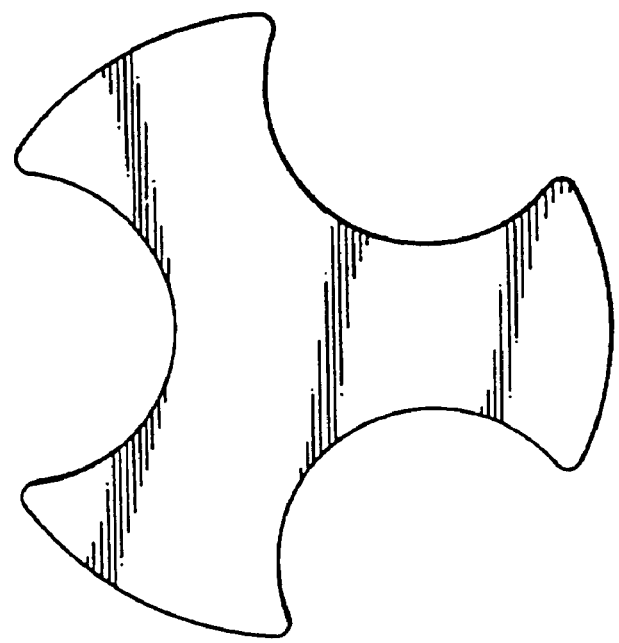

| | | | | |
|---|---|---|---|---|
| 4,471,061 | A | * | 9/1984 | Shaw et al. .................... 502/34 |
| 4,547,588 | A | * | 10/1985 | Khoobiar .................... 562/535 |
| 4,656,157 | A | * | 4/1987 | Hofmann et al. ........... 502/439 |
| 5,072,052 | A | * | 12/1991 | Boeck et al. ................ 568/479 |
| 5,168,090 | A | * | 12/1992 | Ebner et al. ................ 502/209 |
| 6,171,571 | B1 | * | 1/2001 | Bedard et al. ............ 423/594.7 |
| 6,383,976 | B1 | * | 5/2002 | Arnold et al. ............... 502/311 |
| 6,444,845 | B1 | * | 9/2002 | Karim et al. ............... 562/535 |
| 6,525,217 | B1 | * | 2/2003 | Unverricht et al. ......... 562/544 |
| 6,740,779 | B1 | * | 5/2004 | Tenten et al. ................ 562/598 |

FOREIGN PATENT DOCUMENTS

| | | |
|---|---|---|
| DE | 1 046 957 | 12/1958 |
| DE | 33 00 044 | 7/1983 |
| DE | 44 31 949 | 3/1995 |
| DE | 44 31 957 | 3/1995 |
| DE | 44 05 059 | 8/1995 |
| DE | 198 15 279 | 10/1999 |
| DE | 199 48 523 | 4/2001 |
| DE | 100 34 825 | 1/2002 |
| DE | 100 46 672 | 3/2002 |
| DE | 100 51 419 | 4/2002 |
| DE | 100 59 713 | 6/2002 |
| DE | 100 63 162 | 6/2002 |
| EP | 0 092 097 | 10/1983 |
| EP | 0 184 790 | 6/1986 |
| EP | 0 253 409 | 1/1988 |
| EP | 0 355 664 | 2/1990 |
| EP | 0 417 723 | 3/1991 |
| EP | 0 608 838 | 8/1994 |
| EP | 0 700 893 | 3/1996 |
| EP | 0 714 700 | 6/1996 |
| WO | 92/05870 | 4/1992 |
| WO | 97/36849 | 10/1997 |

* cited by examiner

HETEROGENICALLY CATALYSED GAS-PHASE PARTIAL OXIDATION METHOD FOR PRECURSOR COMPOUNDS OF (METH)ACRYLIC ACID

The present invention relates to a process for the heterogeneously catalyzed gas-phase partial oxidation of a precursor compound of (meth)acrylic acid to (meth)acrolein and/or (meth)acrylic acid by passing a reaction gas starting mixture comprising the precursor compound, molecular oxygen and, if required, a gas which is inert with respect to the catalytic gas-phase partial oxidation, at elevated temperatures, through a fixed catalyst bed which contains, as the catalyst, a mixed oxide active material shaped into a geometric body, this geometric body being a geometric base body into whose surface at least one cavity has been introduced.

In this publication, (meth)acrylic acid is used as abbreviated notation for methacrylic acid or acrylic acid. In this publication, (meth)acrolein is used as abbreviated notation for methacrolein or acrolein.

(Neth)acrylic acid, either as such or in the form of its esters, is important in particular for the preparation of polymers for a very wide range of applications, for example for use as adhesives.

In this publication, precursor compounds of (meth)acrylic acid are understood very generally as meaning organic compounds from which (meth)acrylic acid is obtainable by heterogeneously catalyzed gas-phase partial oxidation. They are usually alkanes, alkanols, alkenes or alkenals which contain 3 or 4 carbon atoms. (Meth)acrylic acid is particularly advantageously obtainable, for example, by heterogeneously catalyzed gas-phase partial oxidation of propane, propene, tert-butanol, isobutene, isobutane, isobutyraldehyde or (meth)acrolein. However, other possible precursor compounds are those from which the actual $C_3$-/$C_4$-precursor compound is only formed as an intermediate during the heterogeneously catalyzed gas-phase partial oxidation. An example is the methyl ether of tert-butanol.

In the heterogeneously catalyzed gas-phase partial oxidation, the precursor compounds described above are passed, as starting gases, as a rule diluted with inert gases such as molecular oxygen, CO, $CO_2$, inert hydrocarbons and/or steam, as a mixture with molecular oxygen, at elevated temperatures (usually from about 200 to 450° C.) and, if required, superatmospheric pressure, over transition metal mixed oxide active materials (e.g. containing Mo, Cu and P, or Mo, Bi and Fe, or Mo, V and W, or Mo, V, Te and Nb (where P is not mentioned, it is as a rule not present)) and are converted by oxidation either directly into (meth)acrylic acid or, in a first step, into its precursor compound (meth)acrolein (cf. for example DE-A 4 405 059, EP-A 253 409, EP-A 92097, DE-A 4 431 957, DE-A 4 431 949, CN-A 1 105 352, WO 97/36849, EP-A 608 838, EP-A 714 700, EP-A 700 893, EP-A 700 714, DE-A 19 815 279, DE-A 10 046 672 and DE-A 10 034 825).

The mixed oxide active materials are shaped into moldings having a very wide range of geometries and the moldings are combined to give a fixed bed through which the reaction gas starting mixture containing the precursor compound is passed at elevated temperatures. During contact with the mixed oxide active material, the desired partial oxidation takes place. If required, the catalyst moldings may also be diluted with inert moldings.

The shaping of the mixed oxide active material can be effected, for example, by compacting mixed oxide active material in powder form to give the desired catalyst geometry (for example by tabletting or extrusion). The resulting catalysts are referred to as unsupported catalysts. For the production of unsupported catalysts, if necessary assistants, e.g. graphite or stearic acid as lubricants and/or molding assistants and reinforcing agents, such as microfibers of glass, asbestos, silicon carbide or potassium titanate, may be present in addition to the mixed oxide catalyst active material in powder form.

Of course, the shaping can also be effected, for example, by applying mixed oxide active material in powder form to preshaped inert or active catalyst supports of suitable geometry. Coated catalysts are obtained thereby.

The shaping methods described can also be used starting from precursor materials of the mixed oxide active materials. The conversion into the active catalysts is effected as a rule afterward by thermal treatment at elevated temperatures.

Finally, the supported catalysts in which the metal oxide active material is absorbed into the pores of inert supports and/or produced therein may also be mentioned. Detailed descriptions of processes for the production of catalyst moldings of mixed oxide catalyst materials suitable according to the invention are to be found, for example, in EP-A 700 893, DE-A 10 063 162, DE-A 10 046 957, DE-A 19 948 523, EP-A 700 714, EP-A 417 723, DE-A 3300044, EP-A 552 287, EP-A 714 700, DE-A 10 059 713 and DE-A 10 051 419.

The catalyst moldings, either as such or as a mixture with inert moldings (for example the inert supports which can be used for the production of coated catalysts), can be converted into fixed catalyst beds. These fixed catalyst beds may be present, for example, in the tubes of tube-bundle reactors (cf. for example EP-A 700 893 and EP-A 700 714) or on the trays of tray reactors.

Spheres and cylinders are recommended as typical geometries for the unsupported catalyst, coated catalyst and supported catalyst moldings in the relevant prior art for the relevant gas-phase partial oxidations.

Very recently the use of catalyst moldings whose geometric body is a ring, i.e. a cylinder (as geometric base body) having a tube introduced into its surface as a cavity was also recommended for the process for the heterogeneously catalyzed gas-phase partial oxidation of precursor compounds of (meth)acrylic acid to (meth)acrolein and/or (meth)acrylic acid (cf. for example DE-A 19 948 523, DE-A 10 063 162, EP-A 184 790, DE-C 3300044 and EP-A 714 700).

In a similar manner, EP-A 417 723 and EP-A 355 664 also recommend the use of geometric catalyst bodies which correspond to a geometric base body into whose surface at least one cavity has been introduced. For example, cylinders, cubes or prisms are considered as possible geometric base bodies.

However, the disadvantage of the abovementioned geometric catalyst bodies which are recommended in the prior art for the process for the heterogeneously catalyzed gas-phase partial oxidation of precursor compounds of (meth)acrylic acid to (meth)acrolein and/or (meth)acrylic acid and which differ from spheres and cylinders is that, in all cases, either the ratio of the volume of the geometric catalyst body ($V_B$) to the volume of the geometric base body ($V_{BA}$), i.e. $V_B:V_{BA}$, is >0.6 and/or the ratio of the external surface area of the geometric catalyst body ($A_B$) to $V_B$, i.e. $A_B:V_B$, is <22 $cm^{-1}$.

This is disadvantageous in that the selectivity of the formation of the desired products achieved using such geometric catalyst bodies is not completely satisfactory.

It is an object of the present invention to provide a process for the heterogeneously catalyzed gas-phase partial oxidation of a precursor compound of (meth)acrylic acid to (meth)acrolein and/or (meth)acrylic acid by passing a reaction gas starting mixture comprising the precursor compound, molecular oxygen and, if required, a gas which is inert with respect to the catalytic gas-phase partial oxidation, at elevated temperatures, through a fixed catalyst bed which contains, as the catalyst, a mixed oxide active material shaped into a geometric body, this geometric body being a geometric base body into whose surface at least one cavity has been introduced, which process ensures improved selectivity with respect to the formation of the desired products.

We have found that this object is achieved by a process for the heterogeneously catalyzed gas-phase partial oxidation of a precursor compound of (meth)acrylic acid to (meth)acrolein and/or (meth)acrylic acid by passing a reaction gas starting mixture comprising the precursor compound, molecular oxygen and, if required, a gas which is inert with respect to the catalytic gas-phase partial oxidation, at elevated temperatures, through a fixed catalyst bed which contains, as the catalyst, a mixed oxide active material shaped into a geometric body, this geometric body being a geometric base body into whose surface at least one cavity has been introduced, wherein the ratio of the volume of the geometric body $V_B$ to the volume of the geometric base body $V_{BA} \leq 0.63$ and the ratio of the external surface area of the geometric body $A_B$ to $V_B \geq 22$ cm$^{-1}$.

According to the invention, $A_B$ to $V_B$ may thus be $\geq 23$ cm$^{-1}$ or $\geq 24$ cm$^{-1}$ or $\geq 25$ cm$^{-1}$ or $\geq 26$ cm$^{-1}$ or $\geq 27$ cm$^{-1}$.

In the novel process, the ratio of $A_B$ to $V_B$ is as a rule $\leq 30$ cm$^{-1}$.

Furthermore, the ratio $V_B:V_{BA}$ may be, according to the invention, $\leq 0.62$ or $\leq 0.61$ or $\leq 0.60$ or $\leq 0.58$ or $\leq 0.56$ or $\leq 0.54$ or $\leq 0.52$ or $\leq 0.50$ or $\leq 0.48$ or $\leq 0.45$. In the novel process, as a rule $V_B:V_{BA}$ is $\geq 0.30$, frequently $\geq 0.35$ or $\geq 0.40$.

According to the invention, it is advantageous if $A_B$ to $V_B$ is very large and $V_B:V_{BA}$ is very small.

According to the invention, it is important that $V_B$, $V_{BA}$ and $A_B$ are those volumes and surface areas which the eye is capable of perceiving visually when viewing the geometric body, i.e. internal volumes and surface areas which originate from finely divided pores and/or cracks in the material of the geometric body are not included in $V_B$, $V_{BA}$ and $A_B$.

In the novel process, preferably at least 25% (of the number), better at least 50%, especially at least 75%, particularly preferably 100%, of the totality of the mixed oxide material contained in the fixed catalyst bed are shaped into geometric bodies for which the abovementioned conditions are fulfilled, i.e. for which $V_B:V_{BA} \leq 0.63$ and for which $A_B$ to $V_B \geq 22$ cm$^{-1}$. If the fixed catalyst bed used for the novel process additionally contains inert moldings for the purpose of dilution, it is preferable, according to the invention, if furthermore at least 25% (of the number), better at least 50%, especially at least 75%, particularly preferably at least 100%, of all inert moldings present are geometric bodies for which the abovementioned conditions are fulfilled, i.e. for which $V_B:V_{BA} \leq 0.63$ and for which $A_B$ to $V_B \geq 22$ cm$^{-1}$.

Suitable geometric base bodies for the novel process are all those which are discussed in EP-A 552 287. These are in particular cylinders, pyramids, cones, cubes, right parallelepipeds, prisms, spheres, truncated cones and truncated pyramids.

Figure 1A:
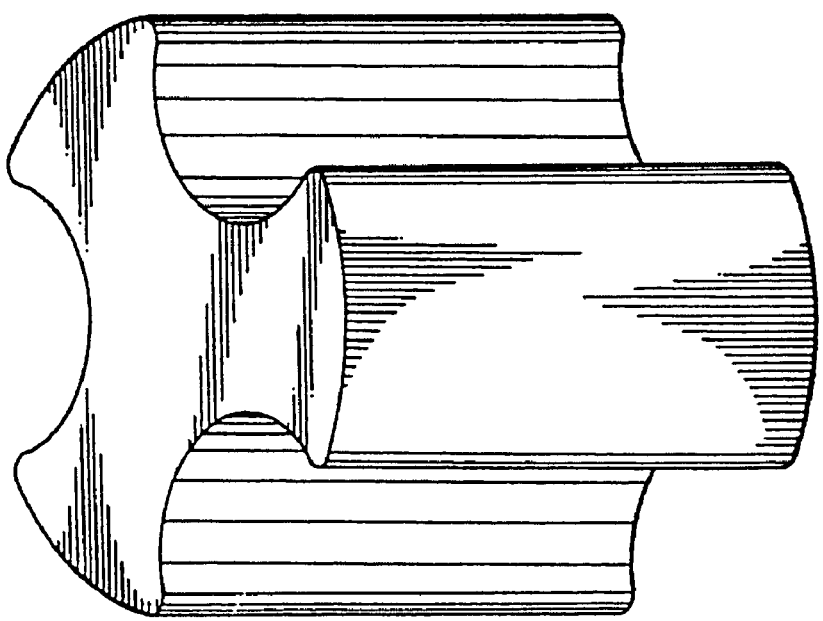

The figures attached to this publication show some novel geometric bodies which are suitable in principle. These are specifically as follows:

FIGS. 1A,B: cylinder as geometric base body; cavities as rounded grooves running substantially perpendicularly from top to bottom, introduced equidistantly into the surface of the base body; FIG. 1B shows the view from above.

Figure 2B:
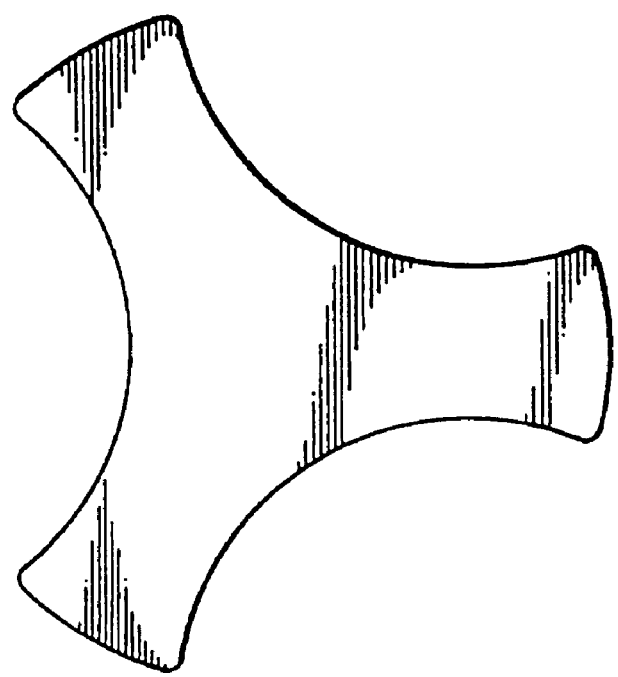
Figure 2A:
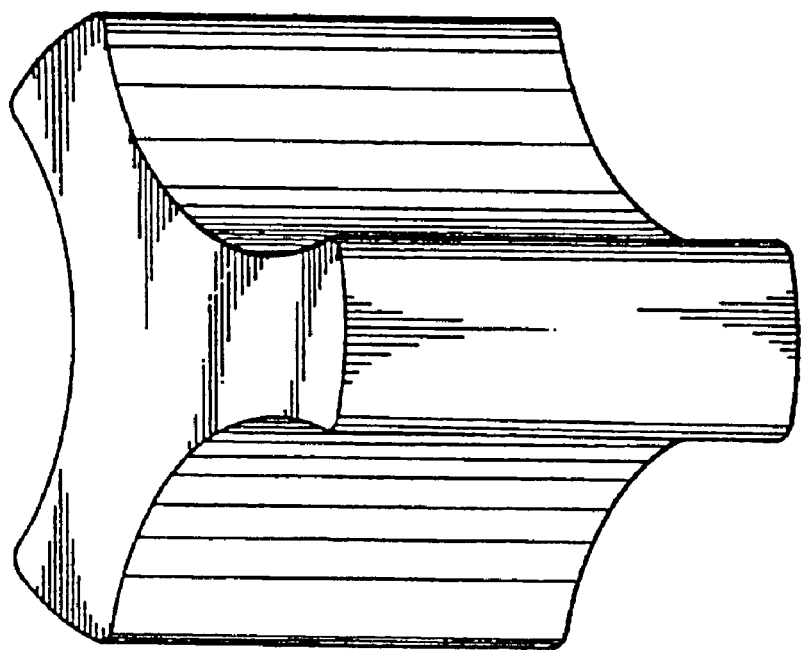

FIGS. 2A,B: this figure shows a variation of the geometry shown in FIGS. 1A,B.

Figure 3B:
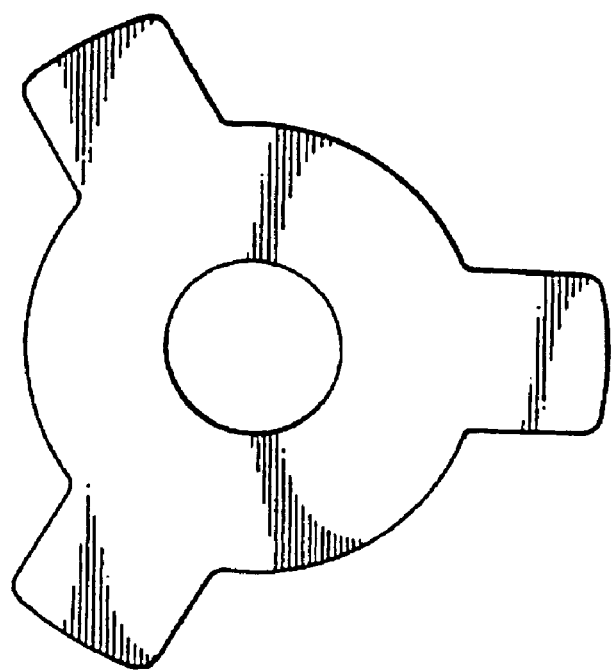
Figure 3A:
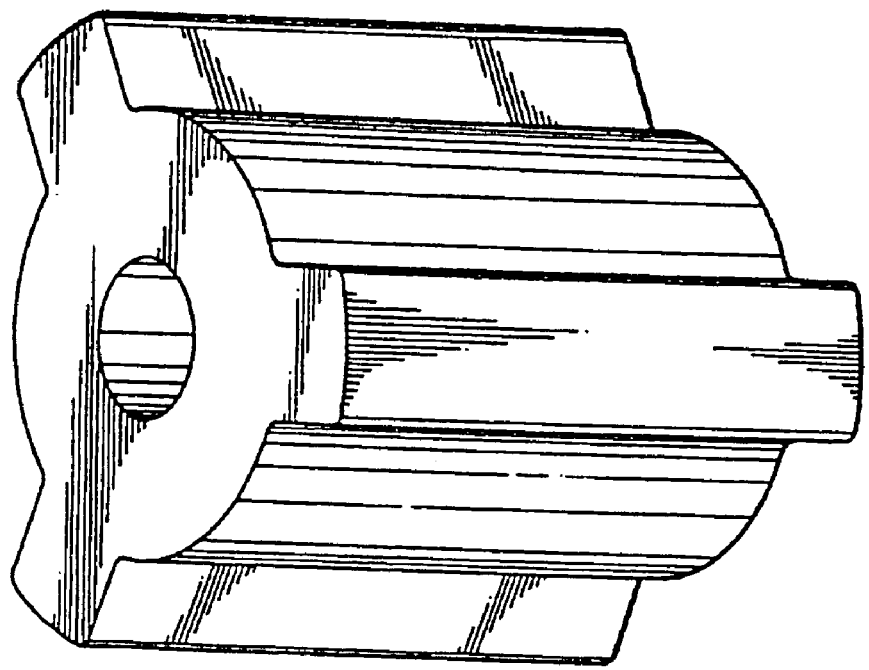

FIGS. 3A,B: this figure shows a variation of the geometry shown in FIGS. 1A,B and additionally contains a central hole.

Figure 4B:
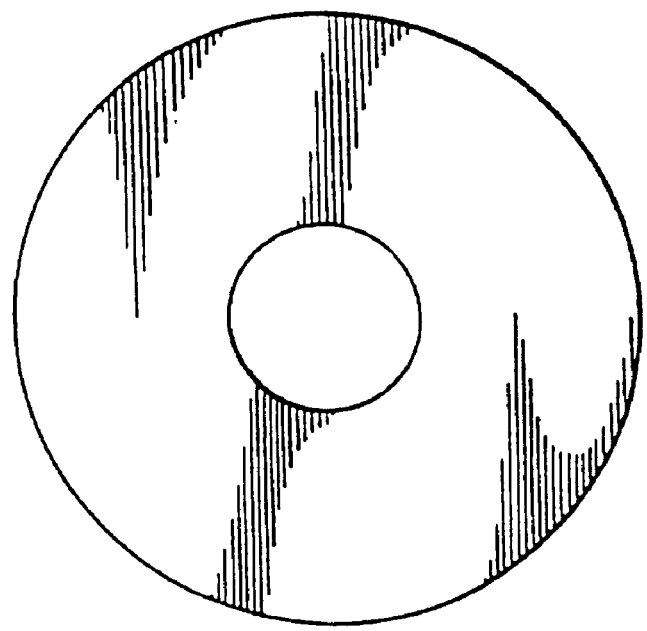
Figure 4A:
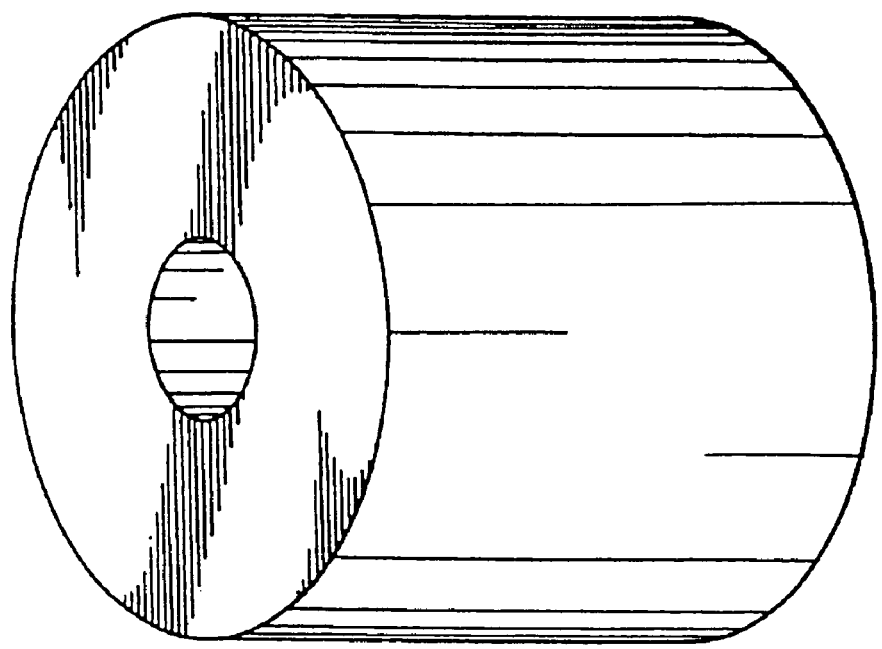

FIGS. 4A,B: cylinder as geometric base body; cavity introduced as central hole. FIG. 4B shows the view from above.

Figure 5A:
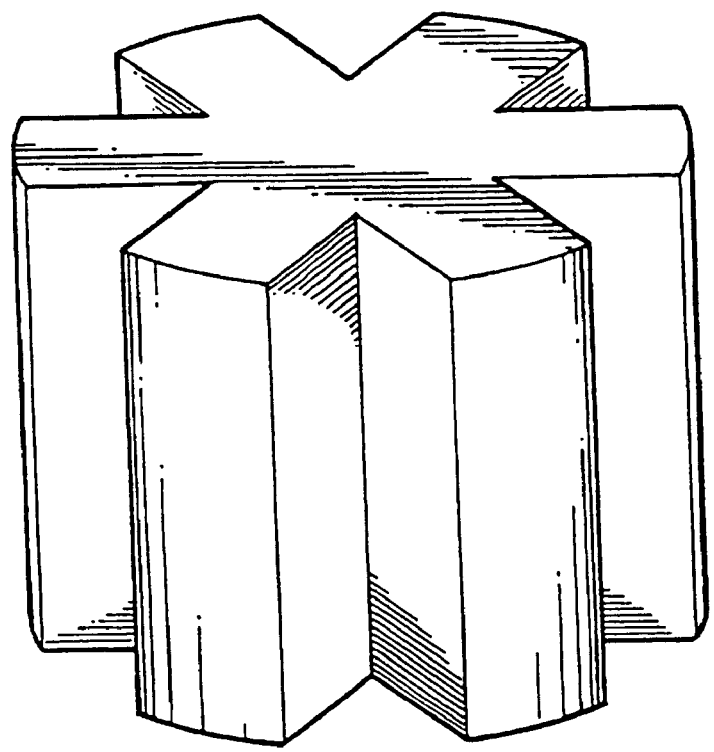
Figure 5B:
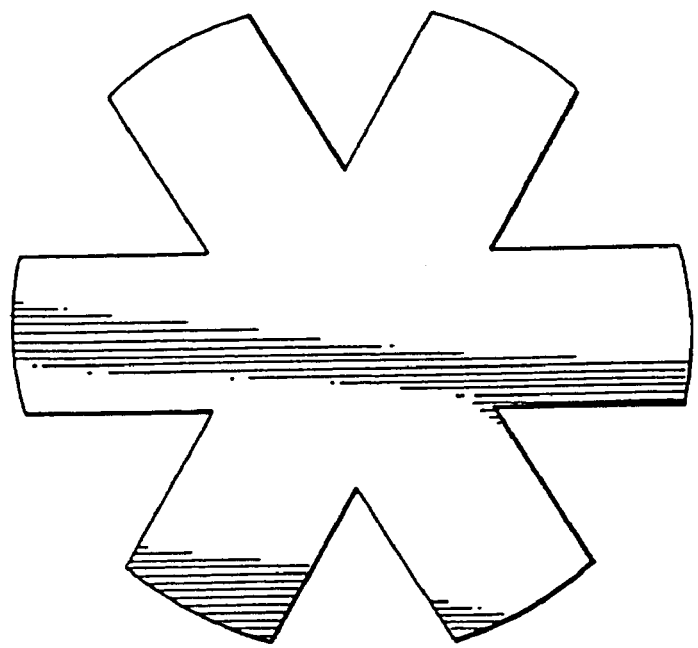

FIGS. 5A,B: this figure shows a variation of the geometry shown in FIGS. 1A,B. Angled grooves.

Figure 6A:
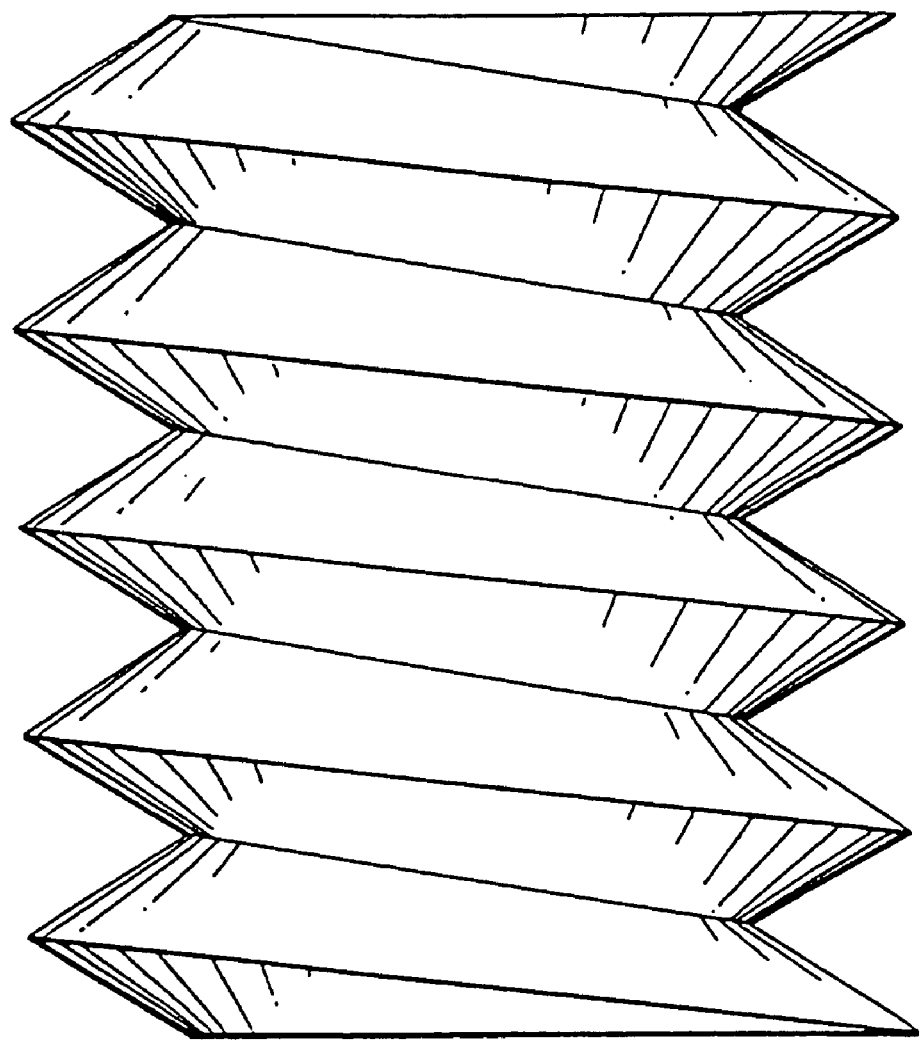
Figure 6B:
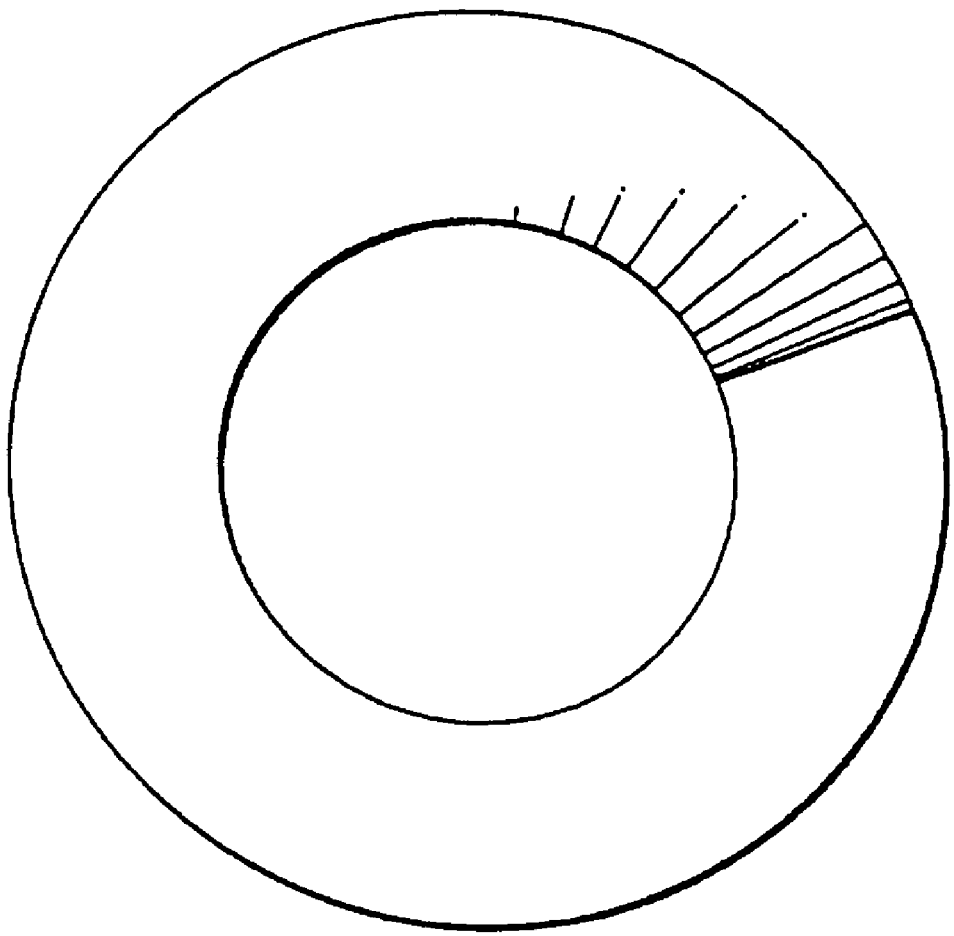

FIGS. 6A,B: cylinder as geometric base body; cavity as central hole and continuously wound spiral introduced into the surface of the base body. FIG. 6B shows the view from above.

Figure 7B:
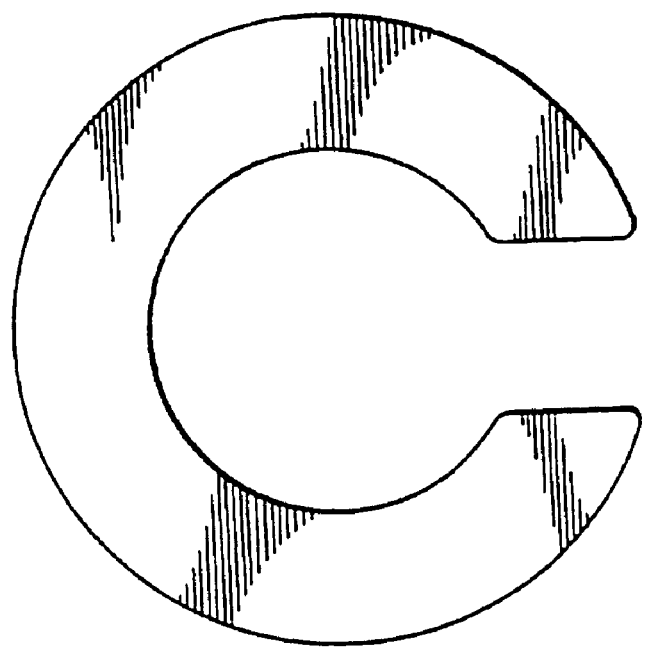
Figure 7A:
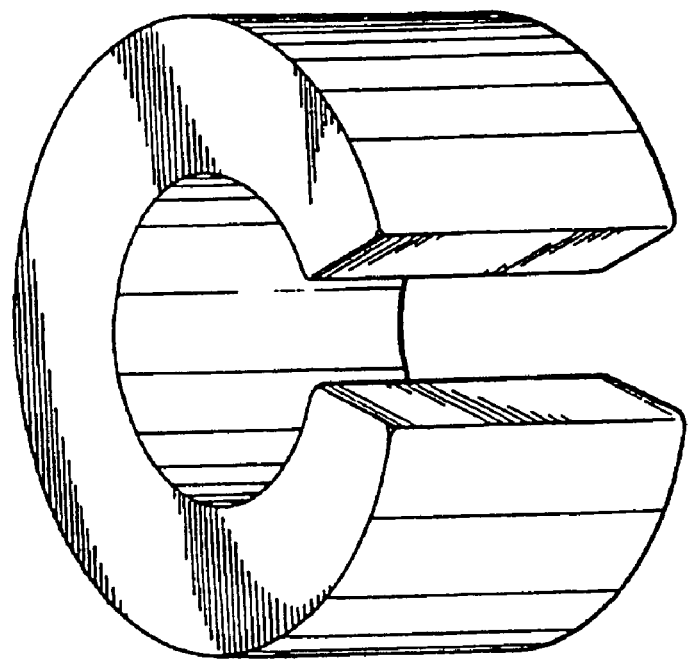

FIGS. 7A,B: cylinder as geometric base body; cavity as a rounded groove running substantially perpendicularly from top to bottom and connected to central hole. FIG. 7B shows the view from above.

Figure 8B:
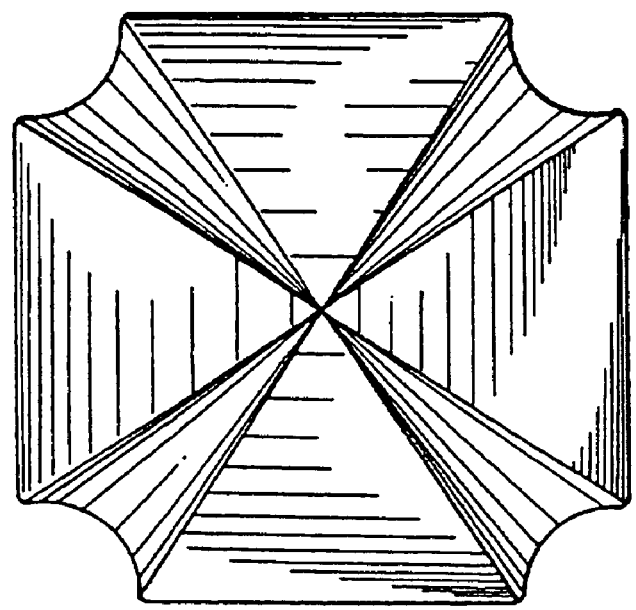
Figure 8A:
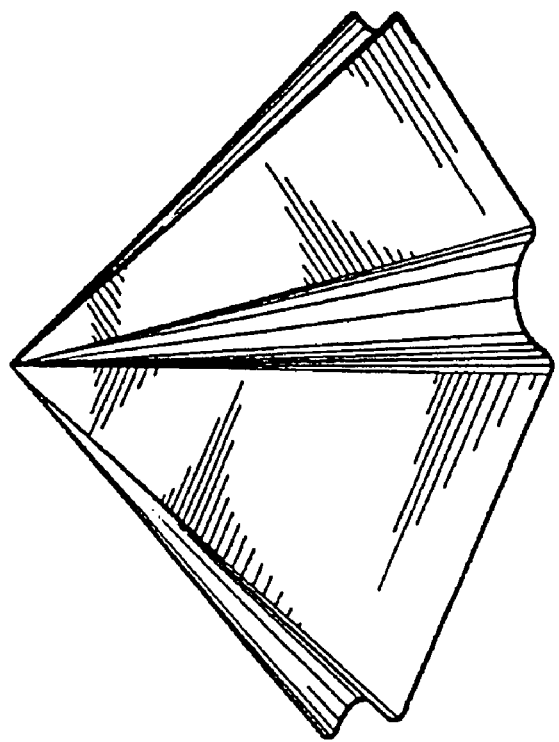

FIGS. 8A,B: pyramid having a square base as base body; cavities as rounded grooves introduced with equal spacing on the outer surface at the edges of the pyramid. FIG. 8B shows the view from above.

Figure 9B:
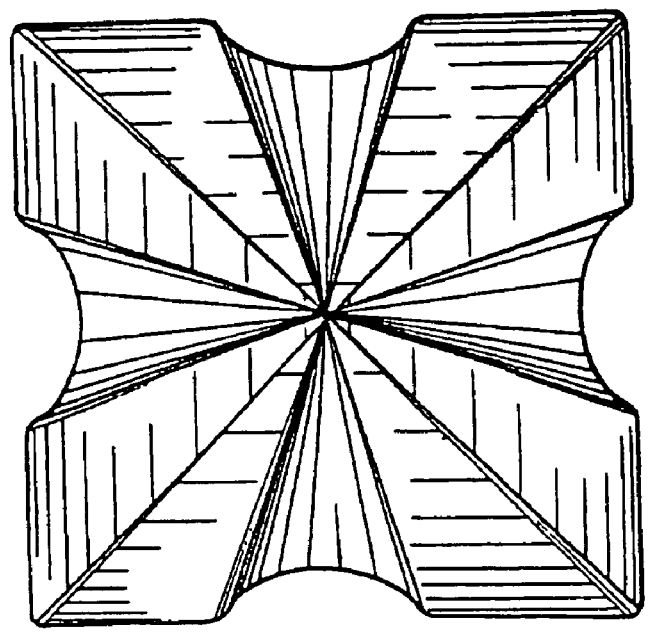
Figure 9A:
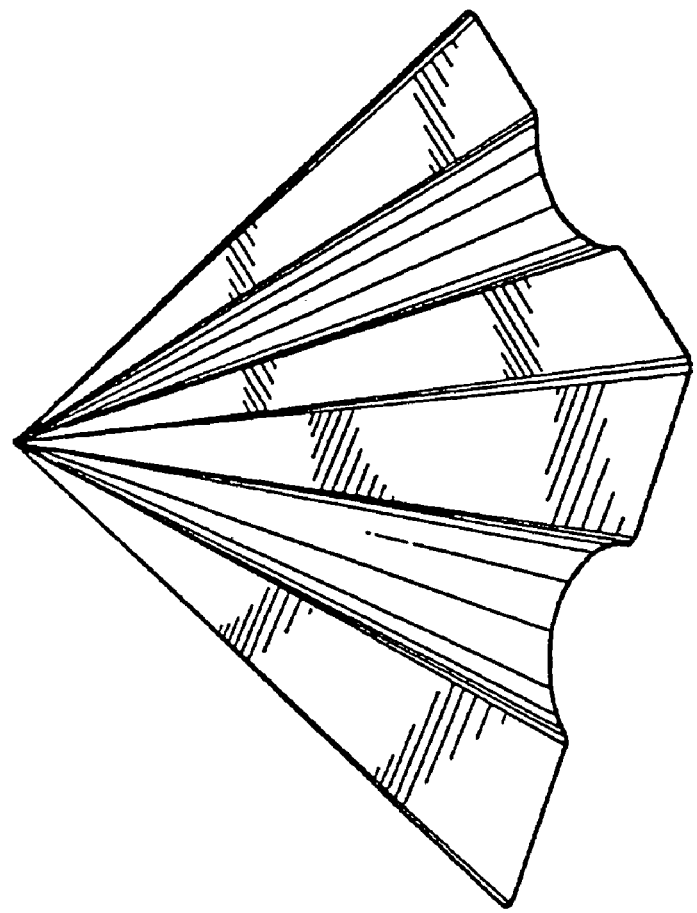

FIGS. 9A,B: pyramid having a square base as base body; cavities as rounded grooves introduced with equal spacing on the outer surface into the sides of the pyramid and running obliquely from top to bottom. FIG. 9B shows the view from above.

Figure 10A:
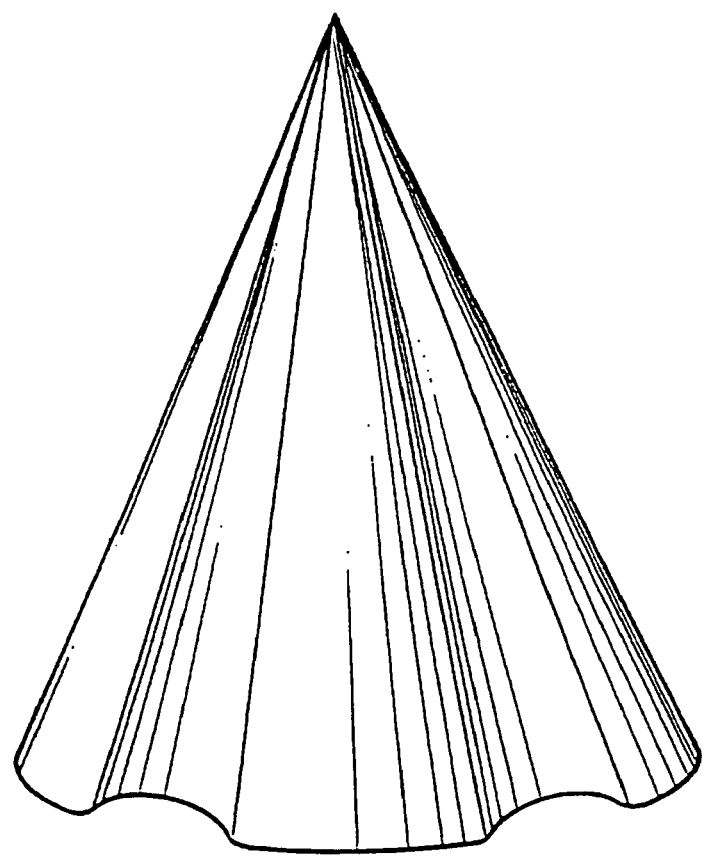
Figure 10B:
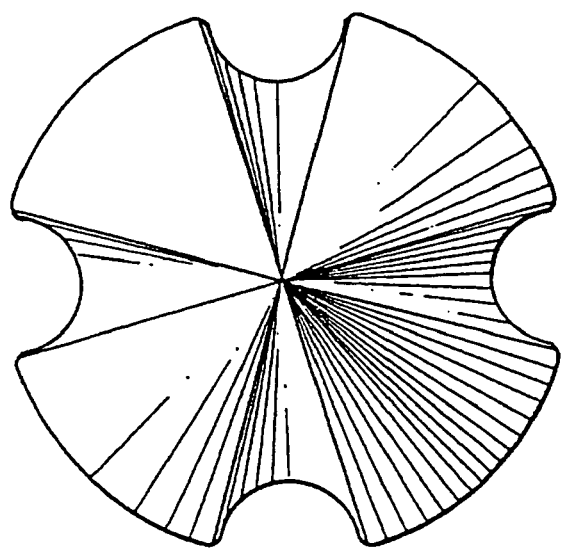

FIGS. 10A,B: cone having a circular base as base body. Cavities as rounded grooves introduced with equal spacing on the outer surface of the cone and running obliquely from top to bottom. FIG. 10B shows the view from above.

Figure 11A:
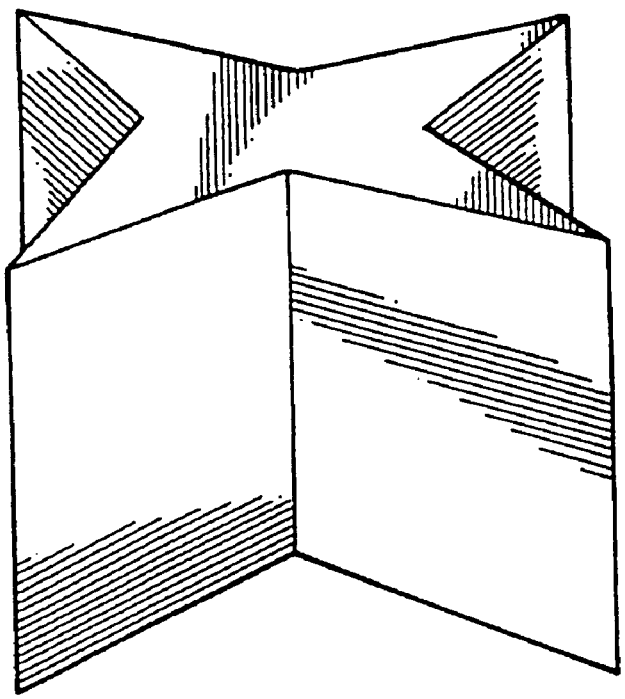
Figure 11B:
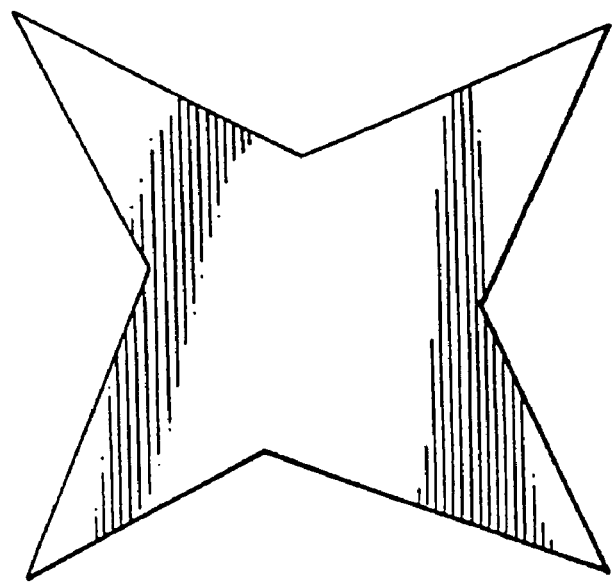

FIGS. 11A,B: cube as base body; cavities as angled grooves introduced with equal spacing on the outer surface of the base body, on the sides, and running substantially perpendicularly from top to bottom. FIG. 11B shows the view from above.

Figure 12A:
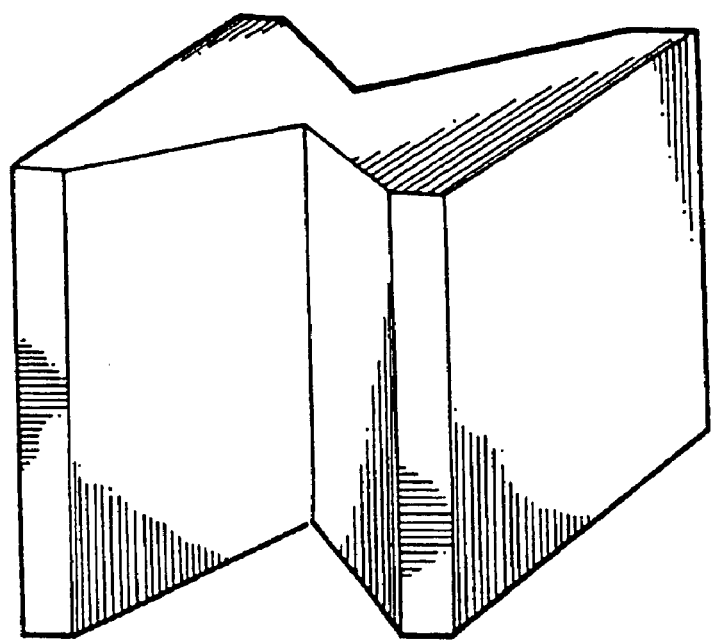
Figure 12B:
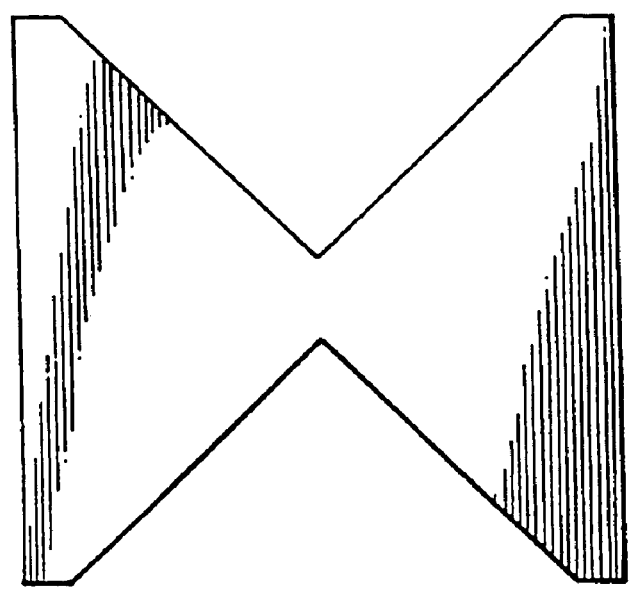

FIGS. 12A,B: cube as base body; cavities as angled grooves on the outer surface, introduced into opposite sides and running substantially perpendicularly from top to bottom. FIG. 12B shows the view from above.

Figure 13A:
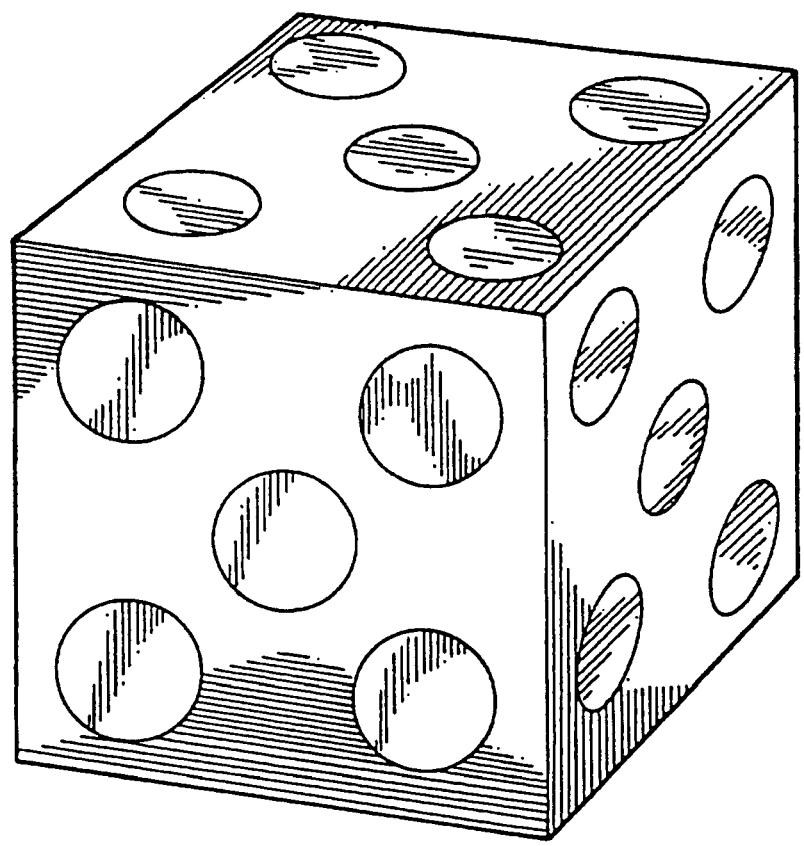
Figure 13B:
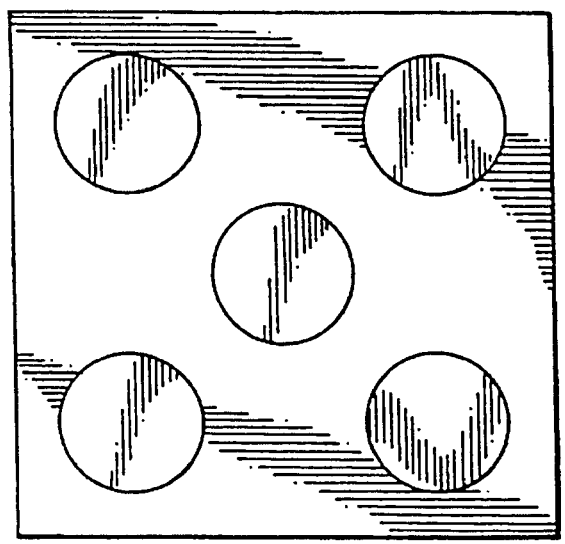

FIGS. 13A,B: cube as base body; cavities as rounded troughs introduced with equal spacing on the outer surface of the base body, on the sides, the upper surface and the lower surface. FIG. 13B shows the view from above.

Figure 14A:
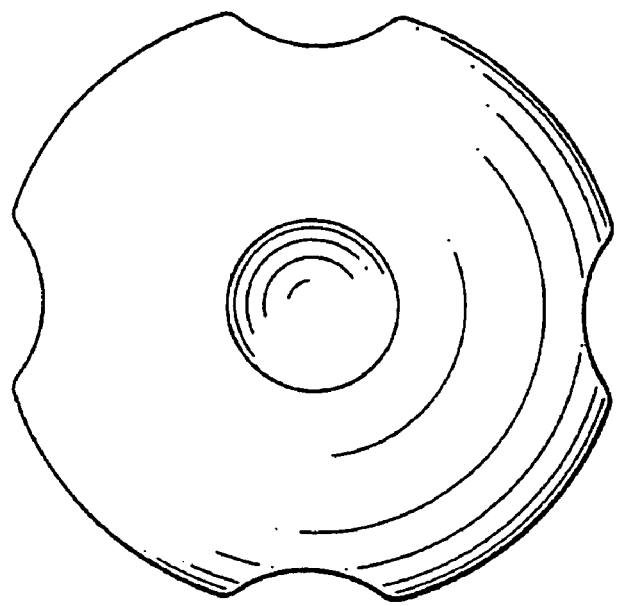
Figure 14B:
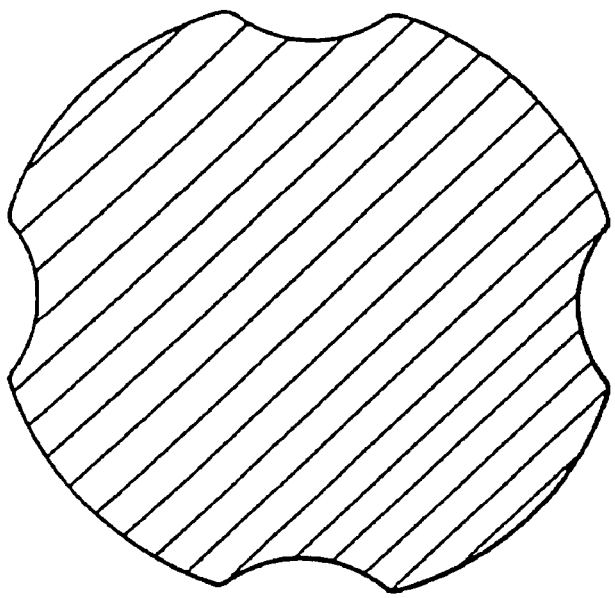

FIGS. 14A,B: sphere as base body; cavities as rounded troughs introduced with equal spacing on the outer surface. FIG. 14B shows the cross-section at the equator.

Mixed oxide catalyst materials shaped into rings are advantageously used as catalysts for the novel process. If they are used in a form diluted with inert moldings, the inert moldings advantageously also have annular geometry. Preferably, the geometries of inert molding and of geometric catalyst body are identical.

According to the invention, the following annular geometries are preferred (in each case external diameter×height× internal diameter):

5.5 mm×3 mm×3.5 mm ($A_B:V_B$=26.7; $V_B:V_{BA}$=0.595);

6 mm×3 mm×4 mm ($A_B:V_B$=26.7; $V_B:V_{BA}$=0.556);

7 mm×3 mm×4.5 mm ($A_B:V_B$=22.7; $V_B:V_{BA}$=0.587);

7 mm×3 mm×5 mm ($A_B:V_B$=26.7; $V_B:V_{BA}$=0.490).

The end faces of the rings may also be curved, as described in EP-A 184 790, for example in such a way that the radius of curvature is preferably from 0.4 to 5 times the external diameter. However, all geometries which are mentioned individually in EP-A 552 287 and for which $A_B:V_B$ is $\geq 22$ and $V_B:V_{BA}$ is $\leq 0.6$ are of course also suitable.

It is furthermore advantageous for the novel process if the empty volume of the fixed catalyst bed used (this is the sum of the volume portions of the fixed catalyst bed which are not occupied by solid when the bed is viewed) is $\geq 50\%$ by volume, based on the total volume of the fixed catalyst bed used (this is the sum of the volume portions of the fixed catalyst bed which are occupied either by solid or by gas when viewed) and based on 25° C. and 1 atm of the bed.

According to the invention, the empty volume of the fixed catalyst bed used may thus be $\geq 52$ or $\geq 55$ or $\geq 57$ or $\geq 60$ or $\geq 62$ or $\geq 65$ or $\geq 67\%$ by volume. In the novel process, the empty volume of the fixed catalyst bed used is as a rule not more than 70% by volume.

If the catalyst body used according to the invention for the novel process has through-holes and if the fixed catalyst bed containing these catalyst bodies is present in the interior of a tube, it is expedient according to the invention if the ratio of internal tube diameter to the longest cross-section of a hole is $\leq 7.5$, preferably $\leq 7$, advantageously $\leq 6.5$, frequently $\leq 6$, often $\leq 5.5$. As a rule, this ratio is $\geq 4$, generally $\geq 4.5$, often $\geq 5$.

The novel process is particularly advantageous when the mixed oxide active materials used are such that, in a single pass through the fixed catalyst bed in the novel process, a conversion of the precursor compound of (meth)acrylic acid of $\geq 90$ mol % results, the selectivity of the resulting formation of the desired products (meth)acrolein and/or (meth)acrylic acid frequently being at least 50, preferably at least 75, particularly preferably at least 85, mol %.

The novel process is particularly suitable for the following heterogeneously catalyzed gas-phase partial oxidations of precursor compounds of (meth)acrylic acid (to be carried out in each case in an oxidation stage):
a) propene to acrolein;
b) propene to acrylic acid;
c) acrolein to acrylic acid;
d) propane to acrolein;
e) propane to acrylic acid;
f) isobutene to methacrolein;
g) isobutene to methacrylic acid;
h) methacrolein to methacrylic acid;
i) isobutane to methacrolein;
j) isobutane to methacrylic acid.

The mixed oxide active materials required as catalysts for these heterogeneously catalyzed gas-phase oxidations and the methods for shaping them into geometric bodies suitable according to the invention are described in the prior art, for example that cited in this publication.

A large number of the mixed oxide active materials suitable for the heterogeneously catalyzed gas-phase partial oxidation of propene to acrolein can be subsumed under the formula I $$Mo_{12}Bi_aFe_bX^1_cX^2_dX^3_eX^4_fO_n \quad (I)$$

where
$X^1$ is nickel and/or cobalt,
$X^2$ is thallium, an alkali metal and/or an alkaline earth metal,
$X^3$ is zinc, phosphorus, arsenic, boron, antimony, tin, cerium, lead and/or tungsten,
$X^4$ is silicon, aluminum, titanium and/or zirconium, a is from 0.5 to 5,
b is from 0.01 to 5, preferably from 2 to 4,
c is from 0 to 10, preferably from 3 to 10,
d is from 0 to 2, preferably from 0.02 to 2,
e is from 0 to 8, preferably from 0 to 5,
f is from 0 to 10 and
n is a number which is determined by the valency and frequency of the elements other than oxygen in I.

They are obtainable in a manner known per se (cf. for example DE-A 4023239) and can be used, according to the invention, for example either as such in the shape of rings or in the form of annular coated catalyst, i.e. inert supports preshaped into rings and coated with the mixed oxide active material.

In principle, suitable mixed oxide active materials I can be prepared in a simple manner by producing, from suitable sources of their elemental constituents, a very intimate, preferably finely divided dry blend having a composition corresponding to their stoichiometry and calcining said dry blend at from 350 to 650° C. The calcination can be carried out either under inert gas or under an oxidizing atmosphere, e.g. air (mixture of inert gas and oxygen) or under a reducing atmosphere (for example a mixture of inert gas, $NH_3$, CO and/or $H_2$). The duration of calcination may be from a few minutes to a few hours and usually decreases with increasing temperature. Suitable sources of the elemental constituents of the mixed oxide active materials I are those compounds which are already oxides and/or those compounds which can be converted into oxides by heating, at least in the presence of oxygen.

In addition to the oxides, such suitable starting compounds are in particular halides, nitrates, formates, oxalates, citrates, acetates, carbonates, amine complexes, ammonium salts and/or hydroxides (compounds, such as $NH_4OH$, $(NH_4)_2CO_3$, $NH_4NO_3$, $NH_4CHO_2$, $CH_3COOH$, $NH_4CH_3CO_2$ and/or ammonium oxalate, which decompose and/or can be decomposed at the latest during the subsequent calcination into compounds escaping completely in gaseous form may additionally be incorporated into the intimate dry blend).

The thorough mixing of the starting compounds for the preparation of mixed oxide active materials I can be effected in dry or in wet form. If it is effected in dry form, the starting compounds are expediently used in the form of finely divided powders and, after mixing and, if required, compaction, are subjected to the calcination. However, the thorough mixing is preferably effected in wet form. Usually, the starting compounds are mixed with one another in the form of an aqueous solution and/or suspension. Particularly intimate dry blends are obtained in the mixing process described when the starting materials used are exclusively sources of the elemental constituents present in dissolved form. A preferably used solvent is water. The aqueous material obtained is then dried, the drying process preferably being carried out by spray-drying of the aqueous mixture at outlet temperatures of from 100 to 150° C.

The mixed oxide active materials of the formula I can be used for the novel process, for example, in the form of an annular catalyst geometry, where the shaping may be effected before or after the final calcination. For example, annular unsupported catalysts can be produced from the powder form of the active material or its uncalcined and/or partially calcined precursor material by compaction to give the desired catalyst geometry (for example by extrusion), and, if required, assistants, e.g. graphite or stearic acid as lubricants and/or molding assistants and reinforcing agents such as microfibers of glass, asbestos, silicon carbide or potassium titanate, may be added.

The shaping of the pulverulent mixed oxide active material or its pulverulent, still uncalcined and/or partially calcined precursor material can of course also be carried out by application to inert catalyst supports preshaped into annular form. The coating of the annular supports for the production of the coated catalysts is carried out as a rule in a suitable rotatable container, as disclosed, for example, in DE-A 2909671, EP-A 293859 or EP-A 714700. For coating the annular supports the powder material to be applied on the support is expediently moistened and, after application, is dried, for example by means of hot air. The coat thickness of the powder material applied to the annular supports is expediently chosen to be in the range from 10 to 1000 μm, preferably from 50 to 500 μm, particularly preferably from 150 to 250 μm.

The support materials used may be conventional porous or nonporous aluminas, silica, thorium dioxide, zirconium dioxide, silicon carbide or silicates, such as magnesium silicate or aluminum silicate. Supports having pronounced surface roughness are preferred. The use of substantially nonporous, annular steatite supports having a rough surface is suitable. The fineness of the catalytically active oxide materials to be applied to the surface of the support is of course adapted to the desired coat thickness (cf. EP-A 714 700).

Alternatively, for the purpose of shaping, the annular support can also be impregnated with a solution and/or suspension containing the starting compounds of the elemental constituents of the relevant mixed oxide active material, dried and finally, as described, calcined to give supported catalysts.

Advantageous mixed oxide active materials to be used according to the invention for a novel partial oxidation of propene to acrolein are furthermore materials of the formula II $$[Y^1{}_a Y^2{}_b O_{x'}]_p [Y^3{}_{c'} Y^4{}_{d'} Y^5{}_{e'} Y^6{}_{f'} Y^7{}_{g'} Y^2{}_{h'} O_{y'}]_q \qquad (II),$$

where
$Y^1$ is bismuth, tellurium, antimony, tin and/or copper,
$Y^2$ is molybdenum and/or tungsten,
$Y^3$ is an alkali metal, thallium and/or samarium,
$Y^4$ is an alkaline earth metal, nickel, cobalt, copper, manganese, zinc, tin, cadmium and/or mercury,
$Y^5$ is iron, chromium, cerium and/or vanadium,
$Y^6$ is phosphorus, arsenic, boron and/or antimony,
$Y^7$ is a rare earth metal, titanium, zirconium, niobium, tantalum, rhenium, ruthenium, rhodium, silver, gold, aluminum, gallium, indium, silicon, germanium, lead, thorium and/or uranium,
a' is from 0.01 to 8,
b' is from 0.1 to 30,
c' is from 0 to 4,
d' is from 0 to 20,
e' is from 0 to 20,
f' is from 0 to 6,
g' is from 0 to 15,
h' is from 8 to 16,
x' and y' are each numbers which are determined by the valency and frequency of the elements other than oxygen in II and
p and q are numbers whose ratio p/q is from 0.1 to 10, containing three-dimensional regions of the chemical composition $Y^1{}_{a'} Y^2{}_{b'} O_{x'}$ which are delimited from their local environment owing to their composition differing from their local environment and whose maximum diameter (longest distance passing through the center of gravity of the region and connecting two points present on the surface (interface) of the region) is from 1 nm to 100 μm, frequently from 10 nm to 500 nm or from 1 μm to 50 or 25 μm.

Particularly advantageous novel mixed oxide active materials II are those in which $Y^1$ is bismuth.

Among these in turn those which correspond to the formula III $$[Bi_{a''} Z^2{}_{b''} O_{x''}]_{p''} [Z^2{}_{12} Z^3{}_{c''} Z^4{}_{d''} Fe_{e''} Z^5{}_{f''} Z^6{}_{g''} Z^7{}_{h''} O_{y''}]_q \qquad (III),$$

where
$Z^2$ is molybdenum and/or tungsten,
$Z^3$ is nickel and/or cobalt,
$Z^4$ is thallium, an alkali metal and/or an alkaline earth metal,
$Z^5$ is phosphorus, arsenic, boron, antimony, tin, cerium and/or lead,
$Z^6$ is silicon, aluminum, titanium and/or zirconium,
$Z^7$ is copper, silver and/or gold,
a" is from 0.1 to 1,
b" is from 0.2 to 2,
c" is from 3 to 10,
d" is from 0.02 to 2,
e" is from 0.01 to 5, preferably from 0.1 to 3,
f" is from 0 to 5,
g" is from 0 to 10,
h" is from 0 to 1,
x" and y" are each numbers which are determined by the valency and frequency of the elements other than oxygen in III,
p" and q" are each numbers whose ratio p"/q" is from 0.1 to 5, preferably from 0.5 to 2, are preferred, very particularly preferred materials III being those in which $Z^2{}_{b''}$ is (tungsten)$_{b''}$ and $Z^2{}_{12}$ is (molybdenum)$_{12}$.

It is also advantageous if at least 25 mol % (preferably at least 50, particularly preferably at least 100, mol %) of the total moiety $[y^1{}_a y^2{}_b O_{x'}]_p$ ($[Bi_{a''} Z^2{}_{b''} O_{x''}]_{p''}$) of the mixed oxide active materials II (mixed oxide active materials III) are present in these mixed oxide active materials in the form of three-dimensional regions of the chemical composition $y^1{}_a y^2{}_b O_{x'}$ ($Bi_{a''} Z^2{}_{b''} O_{x''}$) which are delimited from the local environment owing to their chemical composition differing from their local environment and whose largest diameter is from 1 nm to 100 μm.

Regarding the shaping, the statements made in the case of the mixed oxide active materials I are applicable with regard to the mixed oxide active materials II.

A large number of the mixed oxide active materials suitable for the heterogeneously catalyzed gas-phase partial oxidation of acrolein to acrylic acid can be subsumed under the formula IV $$Mo_{12} V_a X^1{}_b X^2{}_c X^3{}_d X^4{}_e X^5{}_f X^6{}_g O_n \qquad (IV),$$

where
$X^1$ is W, Nb, Ta, Cr and/or Ce,
$X^2$ is Cu, Ni, Co, Fe, Mn and/or Zn,
$X^3$ is Sb and/or Bi,
$X^4$ is one or more alkali metals,
$X^5$ is one or more alkaline earth metals,
$X^6$ is Si, Al, Ti and/or Zr,
a is from 1 to 6,
b is from 0.2 to 4,
c is from 0.5 to 18,
d is from 0 to 40, e is from 0 to 2,
f is from 0 to 4,
g is from 0 to 40 and
n is a number which is determined by the valency and frequency of the elements other than oxygen in IV.

Preferred embodiments within the mixed oxide active materials IV are those which are described by the following meanings of the variables in the formula IV:

$X^1$ is W, Nb, and/or Cr,
$X^2$ is Cu, Ni, Co, and/or Fe,
$X^3$ is Sb,
$X^4$ is Na and/or K,
$X^5$ is Ca, Sr and/or Ba,
$X^6$ is Si, Al, and/or Ti,
a is from 1.5 to 5,
b is from 0.5 to 2,
c is from 0.5 to 3,
d is from 0 to 2,
e is from 0 to 0.2,
f is from 0 to 1 and
n is a number which is deteremined by the valency and frequency of the elements other than oxygen in IV.

However, very particularly preferred mixed oxide active materials IV are those of the formula V $$Mo_{12}V_{a'}Y^1_{b'}Y^2_{c'}Y^5_{f'}Y^6_{g'}O_{n'} \quad (V)$$

where
$Y^1$ is W and/or Nb,
$Y^2$ is Cu and/or Ni,
$Y^5$ is Ca and/or Sr,
$Y^6$ is Si and/or Al,
a' is from 2 to 4,
b' is from 1 to 1.5,
c' is from 1 to 3,
f' is from 0 to 0.5,
g' is from 0 to 8 and
n' is a number which is determined by the valency and frequency of the elements other than oxygen in V.

The mixed oxide active materials (IV) suitable according to the invention are obtainable in a manner known per se, for example disclosed in DE-A 4335973 or in EP-A 714700.

In principle, mixed oxide active materials suitable according to the invention and of the formula IV can be prepared in a simple manner by producing, from suitable sources of their elemental constituents, a very intimate, preferably finely divided dry blend having a composition corresponding to their stoichiometry and calcining said dry blend at from 350 to 600° C. The calcination can be carried out either under inert gas or under an oxidizing atmosphere, e.g. air (mixture of inert gas and oxygen) or under a reducing atmosphere (e.g. a mixture of inert gas and reducing gases such as $H_2$, $NH_3$, CO, methane and/or acrolein or said reducing gases by themselves). The duration of calcination may be from a few minutes to a few hours and usually decreases with increasing temperature. Suitable sources of the elemental constituents of the mixed oxide active materials IV are those compounds which are already oxides and/or those compounds which can be converted into oxides by heating, at least in the presence of oxygen.

The thorough mixing of the starting compounds for the preparation of mixed oxide active materials IV can be effected in dry or in wet form. If it is effected in dry form, the starting compounds are expediently used in the form of finely divided powder and, after mixing and, if required, compaction, are subjected to calcination. However, thorough mixing is preferably effected in wet form.

Usually, the starting compounds are mixed with one another in the form of an aqueous solution and/or suspension. Particularly intimate dry blends are obtained in the mixing process described when the starting materials used are exclusively sources of the elemental constituents present in dissolved form. A preferably used solvent is water. The aqueous material obtained is then dried, the drying process preferably being carried out by spray-drying of the aqueous mixture at outlet temperatures from 100 to 150° C.

The mixed oxide active materials IV suitable according to the invention can be used for the novel process, for example, after being shaped to give annular catalyst geometries, it being possible to effect the shaping before or after the final calcination, in a manner fully corresponding to that in the case of the mixed oxide active materials I. For example, annular unsupported catalysts can be prepared completely analogously from the powder form of the mixed oxide active material or its uncalcined precursor material by compaction to give the desired catalyst geometry (for example by extrusion) where, if required, assistants, e.g. graphite or stearic acid as lubricants and/or molding assistants and reinforcing agents, such as microfibers of glass, asbestos, silicon carbide or potassium titanate, may be added.

The shaping of the pulverulent active material or its pulverulent, still uncalcined precursor material may of course also be effected by application to inert catalyst support preshaped into annular form. The coating of the supports for the production of the coated catalysts is carried out as a rule in a suitable rotatable container, as disclosed, for example, in DE-A 2909671, EP-A 293859 or EP-A 714700.

For coating the supports, the powder material to be applied is expediently moistened and, after the application, is dried, for example by means of hot air. The coat thickness of the powder material applied to the support is expediently chosen to be in the range from 10 to 1000 μm, preferably from 50 to 500 μm, particularly preferably from 150 to 250 μm.

The support materials used may be conventional porous or nonporous aluminas, silica, thorium dioxide, zirconium dioxide, silicon carbide or silicates, such as magnesium silicate or aluminum silicate. The supports having pronounced surface roughness are preferred. The fineness of the catalytically active oxide materials to be applied to the surface of the support is of course adapted to the desired coat thickness (cf. EP-A 714 700).

According to the invention, the mixed oxide active materials IV can of course also be shaped to give annular supported catalysts.

Advantageous mixed oxide active materials to be used according to the invention for the gas-phase partial oxidation of acrolein to acrylic acid are furthermore materials of the formula VI $$[D]_p[E]_q \quad (VI),$$

where
D is $Mo_{12}V_{a''}Z^1_{b''}Z^2_{c''}Z^3_{d''}Z^4_{e''}Z^5_{f''}Z^6_{g''}O_{x''}$,
E is $Z^7_{12}Cu_{h''}H_{i''}O_{y''}$,
$Z^1$ is W, Nb, Ta, Cr and/or Ce,
$Z^2$ is Cu, Ni, Co, Fe, Mn and/or Zn,
$Z^3$ is Sb and/or Bi,
$Z^4$ is Li, Na, K, Rb, Cs and/or H
$Z^5$ is Mg, Ca, Sr and/or Ba,
$Z^6$ is Si, Al, Ti and/or Zr,
$Z^7$ is Mo, W, V, Nb and/or Ta,
a" is from 1 to 8, b" is from 0.2 to 5,
c" is from 0 to 23,
d" is from 0 to 50,
e" is from 0 to 2,
f" is from 0 to 5,
g" is from 0 to 50,
h" is from 4 to 30,
i" is from 0 to 20 and
x" and y" are numbers which are determined by the valency and frequency of the elements other than oxygen in VI and
p and q are numbers which differ from zero and whose ratio p/q is from 160:1 to 1:1, which are obtainable by separately preforming a multimetal oxide material E

$$Z^7{}_{12}Cu_{h''}H_{i''}O_{y''} \quad (E),$$

in finely divided form (starting material 1) and then incorporating the preformed solid starting material 1 into an aqueous solution, an aqueous suspension or a finely divided dry blend of sources of the elements Mo, V, $Z^1$, $Z^2$, $Z^3$, $Z^4$, $Z^5$ and $Z^6$, which contain the abovementioned elements in the stoichiometry D

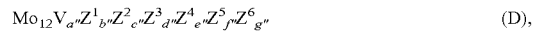
$$Mo_{12}V_{a''}Z^1{}_{b''}Z^2{}_{c''}Z^3{}_{d''}Z^4{}_{e''}Z^5{}_{f''}Z^6{}_{g''} \quad (D),$$

(starting material 2), in the desired ratio p:q, drying any resulting aqueous mixture and calcining the resulting dry precursor material at from 250 to 600° C. before or after it is shaped to give the desired catalyst geometry.

Mixed oxide active materials VI where the preformed solid starting material 1 is incorporated into an aqueous starting material 2 at <70° C. are preferred. A detailed description of the preparation of active material comprising mixed oxide VI appears in, for example, EP-A 668104, DE-A 19736105 and DE-A 19528646.

Regarding the shaping, the statements made in the case of the active materials comprising mixed oxide IV are applicable with regard to the active materials comprising mixed oxide VI.

Mixed oxide active materials particularly suitable for the heterogeneously catalyzed gas-phase partial oxidation of methacrolein to methacrylic acid are disclosed, for example, in DE-A 19 815 279 and in the prior art cited in this publication.

Mixed oxide active materials particularly suitable for the heterogeneously catalyzed gas-phase partial oxidation of propane to acrylic acid are disclosed, for example, in DE-A 10 051 419 and in the prior art cited in this publication.

As in all other cases, the shaping required for the novel process can be effected in the case of the abovementioned mixed oxide active materials too by coating suitable supports or, for example, by extrusion processes.

The novel process is preferably carried out in tube-bundle reactors loaded with the catalyst, as described, for example, in EP-A 700 714 and EP-A 700 893 and in the literature cited in these publications.

In the abovementioned tube-bundle reactors, the catalyst tubes are usually produced from ferritic steel and typically have a wall thickness of from 1 to 3 mm. The internal diameter is as a rule from 20 to 30 mm, frequently from 21 to 26 mm. In terms of application technology, the number of catalyst tubes housed in the tube-bundle container is at least 5000, preferably at least 10000. Frequently, the number of catalyst tubes housed in the reaction container is from 15000 to 30000. Tube-bundle reactors having more than 40000 catalyst tubes tend to be the exception. Inside the container, the catalyst tubes are usually homogeneously distributed, the distribution expediently being chosen so that the distance between the central inner axes of adjacent catalyst tubes (i.e. the catalyst tube spacing) is from 35 to 45 mm (cf. for example EP-B 468 290).

Particularly suitable heat-exchange media are fluid heating media. The use of melts of salts, such as potassium nitrate, potassium nitrite, sodium nitrite and/or sodium nitrate, or of low-melting metals, such as sodium, mercury and alloys of different metals, is particularly advantageous.

Detailed information on the reaction conditions expediently to be maintained for the various novel heterogeneously catalyzed gas-phase partial oxidations of precursor compounds of (meth)acrylic acid is to be found in the prior art cited above.

The novel procedure is particularly suitable for carrying out heterogeneously catalyzed gas-phase partial oxidations of precursor compounds of (meth)acrylic acid which are carried out with high loading of the fixed catalyst bed with the precursor compound, as effected, for example, in DE-A 19 948 523.

Such high-load gas-phase partial oxidations are preferably realized in the multi-zone (preferably two-zone) tube-bundle reactors of DE-A 19 948 523.

The advantage of the novel procedure is primarily an increased selectivity of the formation of the desired products, in particular with the use of high loadings of the fixed catalyst bed with the precursor compound of (meth)acrylic acid.

The size of the catalyst bodies used according to the invention is as a rule such that the longest dimension (longest line connecting two points present on the surface of the catalyst support) is from 2 to 12 mm, frequently from 4 to 8 mm.

EXAMPLES

A) Preparation of a Multimetal Oxide Active Material Suitable for the Heterogeneously Catalyzed Gas-phase Partial Oxidation of Propene to Acrolein and Shaped into Rings of Various Dimensions At 60° C., 213 kg of ammonium heptamolybdate were dissolved in portions in 600 l of water. 0.97 kg of a 46.8% strength by weight aqueous potassium hydroxide solution at 20° C. was stirred into this solution while maintaining the 60° C. (a solution A was obtained). A second solution B was prepared by adding 116.25 kg of an aqueous iron nitrate solution (14.2% by weight of Fe) to 333.7 kg of an aqueous cobalt nitrate solution (12.4% by weight of Co) at 30° C. while stirring. After the end of the addition, stirring was carried out for a further 30 minutes at 30° C. 112.3 kg of an aqueous bismuth nitrate solution (11.2% by weight of Bi) were then stirred in at 60° C. to give the solution B. The solution B was stirred into the solution A at 60° C. in the course of 30 minutes. 15 minutes after the end of the stirring in, 19.16 kg of silica sol (46.80% by weight of $SiO_2$, density: 1.36 to 1.42 g/ml, pH from 8.5 to 9.5, alkali content not more than 0.5% by weight) were added to the resulting slurry at 60° C. Stirring was carried out for a further 15 minutes while maintaining the 60° C. The slurry obtained was then spray-dried by the countercurrent method (gas inlet temperature: 400±10° C., gas outlet temperature: 140±5° C.), a spray-dried powder whose loss on ignition (3 hours at 600° C. under air) was 30% of its weight being obtained.

In each case 1.5% by weight of finely divided graphite (sieve analysis: min. 50% by weight <24 μm, max. 10% by weight >24 μm and <48 μm, max. 5% by weight >48 μm, BET surface area: from 6 to 13 m²/g) were additionally mixed into portions of the resulting spray-dried powder (particle size of the spray-dried powder was about 30 μm).

The dry blend resulting in each case was compacted (compressed) to give hollow cylinders (rings) of different geometries so that the resulting density was about 2.5 mg/mm³ and the resulting lateral compressive strength of the rings was about 10 N.

For the final calcination, in each case 1900 g of the shaped rings were poured into a heatable through-circulation chamber (0.12 m³ internal volume, 2 m³ (S.T.P.) of air/minute). The temperature in the bed was then changed as follows:
increased from 25° C. to 160° C. at 1° C./min.;
then kept at 160° C. for 100 min.;
then increased from 160° C. to 200° C. at 3° C./min;
then kept at 200° C. for 100 min.;
then increased from 200° C. to 230° C. at 2° C./min.;
then kept at 230° C. for 100 min.;
then increased from 230° C. to 270° C. at 3° C./min.;
then kept at 270° C. for 100 min.;
then increased to 380° C. at 1° C./min.;
then kept at 380° C. for 4.5 h;
then increased to 430° C. at 1° C./min.;
then kept at 430° C. for 4.5 h;
then increased to 500° C. at 1° C./min.;
then kept at 500° C. for 9 h;
then cooled to 25° C. in the course of 4 h.
Annular catalyst bodies were obtained.

B) Heterogeneously Catalyzed Gas-phase Partial Oxidation of Propene to Acrolein

A reaction tube (V2A stainless steel, 30 mm external diameter; 2 mm wall thickness; 26 mm internal diameter, length: 439 cm) was loaded from bottom to top, on a catalyst support ledge (44 cm long), first with steatite beads having a rough surface (from 4 to 5 mm diameter; inert material for heating the reaction gas starting mixture) over a length of 30 cm and then in each case with the catalyst rings produced under A) over a length of 270 cm (the fixed catalyst bed), before the loading was completed with the abovementioned steatite beads as a downstream bed over a length of 30 cm. The remaining catalyst tube length was left empty.

That part of the reaction tube which had been loaded with solid was thermostatted by means of 11 cylindrical aluminum blocks which had been cast around the tube, each had a length of 30 cm and was heated by electric heating tapes (comparative experiments using a corresponding reaction tube heated by means of a salt bath through which nitrogen was bubbled showed that thermostatting with the aluminum block was capable of simulating thermostatting with a salt bath). Those ends of the reaction tube which were free of solid were kept at 220° C. with steam under superatmospheric pressure.

The reaction tube described above was continuously fed with a reaction gas starting mixture having the following composition:
6.5% by volume of propene,
3.5% by volume of $H_2O$,
0.5% by volume of CO,
1.2% by volume of $CO_2$,
0.04% by volume of acrolein and
10.7% by volume of $O_2$,
the remaining amount to 100% by volume comprising molecular nitrogen.

The loading of the fixed catalyst bed was chosen as 100 l (S.T.P) of propene/l·h. A small sample of the product gas mixture was taken at the exit for a gas chromatographic analysis. The temperature of all aluminum blocks was set at a standard value in all cases so that the propene conversion in all cases was 95 mol % in a single pass. The temperatures required for this purpose were about 330° C.

The table below shows the selectivity of the acrolein formation ($S_A$) achieved as a function of the catalyst geometry used. The letter C indicates that it is a comparative example, while the letter E shows that it is an example according to the invention.
Other meanings are:
Ex=external diameter,
H=height and
In=internal diameter
of the catalyst ring.

In addition, the table shows, as example E5, the result when a catalyst body having the geometry according to FIG. 1 is used.

The preparation was carried out as in the case of the catalyst rings, except that the precursor material was compressed to give the other geometry.

The diameter and the height of the base body were 4 mm.

The groove depth was about 0.5 mm. The spacing of the groove segment ends was about 0.9 mm.

TABLE

|  | Ex (mm) | H (mm) | In (mm) | $V_B$ (cm³) | $V_{BA}$ (cm³) | $A_B$ (cm²) | $A_B/V_B$ (cm⁻¹) | $V_B/V_{BA}$ | $S_A$ (mol %) |
|---|---|---|---|---|---|---|---|---|---|
| C1 | 5 | 3 | 2 | 0.049 | 0.059 | 0.990 | 20 | 0.84 | 86.4 |
| C2 | 5 | 3 | 2.5 | 0.044 | 0.059 | 1.001 | 22.7 | 0.75 | 87.9 |
| C3 | 5 | 3 | 3 | 0.038 | 0.059 | 1.005 | 26.7 | 0.64 | 89.1 |
| C4 | 5 | 2 | 2 | 0.033 | 0.039 | 0.770 | 23.3 | 0.84 | 85.3 |
| C5 | 5 | 2 | 2.5 | 0.029 | 0.039 | 0.766 | 26.0 | 0.75 | 88 |
| C6 | 5 | 2 | 3 | 0.025 | 0.039 | 0.754 | 30.0 | 0.64 | 89.1 |
| C7 | 5.5 | 3 | 2.5 | 0.057 | 0.071 | 1.131 | 20.0 | 0.79 | 88.3 |
| C8 | 5.5 | 3 | 3 | 0.050 | 0.071 | 1.135 | 22.7 | 0.70 | 90.1 |
| E1 | 5.5 | 3 | 3.5 | 0.042 | 0.071 | 1.131 | 26.7 | 0.59 | 91.2 |
| C9 | 6 | 3 | 3 | 0.064 | 0.085 | 1.272 | 20.0 | 0.75 | 89.6 |
| E2 | 6 | 3 | 4 | 0.047 | 0.085 | 1.257 | 26.7 | 0.56 | 92.2 |
| C10 | 7 | 3 | 3 | 0.094 | 0.115 | 1.571 | 16.7 | 0.82 | 87.6 |
| C11 | 7 | 3 | 4 | 0.078 | 0.115 | 1.555 | 20.0 | 0.67 | 89.8 |
| E3 | 7 | 3 | 4.5 | 0.068 | 0.115 | 1.535 | 22.7 | 0.59 | 91.9 |
| E4 | 7 | 3 | 5 | 0.057 | 0.115 | 1.508 | 26.7 | 0.49 | 92.4 |
| E5 | — | — | — | 0.031 | 0.050 | 0.828 | 27.0 | 0.61 | 92.5 |

We claim:

1. A mixed oxide active material having a geometric body, wherein the geometric body is a geometric base body having at least one cavity,
   wherein the ratio of the volume of the geometric body $V_B$ to the geometric base body $V_{BA} \leq 0.63$ and the ratio of the external surface area of the geometric body $A_B$ to $V_B \geq 22$ cm$^{-1}$, and
   wherein the mixed oxide active material comprises at least one set of elements selected from the group of sets consisting of
   a) the elements Mo, Cu and P;
   b) the elements Mo, Bi and Fe;
   c) the elements Mo, V and W; and
   d) the elements Mo, V, Te and Nb.

2. The mixed oxide active material of claim 1, wherein the $A_B$ to $V_B$ ratio is $\geq 23$ cm$^{-1}$.

3. The mixed oxide active material of claim 1, wherein the $A_B$ to $V_B$ ratio is 24 cm$^{-1}$.

4. The mixed oxide active material of claim 1, wherein the $A_B$ to $V_B$ ratio is $\geq 25$ cm$^{-1}$.

5. The mixed oxide active material of claim 1, wherein the $A_B$ to $V_B$ ratio is $\geq 26$ cm$^{-1}$.

6. The mixed oxide active material of claim 1, wherein the $A_B$ to $V_B$ ratio is $\geq 27$ cm$^{-1}$.

7. The mixed oxide active material of claim 1, wherein the $A_B$ to $V_B$ ratio is from 22 cm$^{-1}$ to 30 cm$^{-1}$.

8. The mixed oxide active material of claim 1, wherein the $V_B$ to $V_{BA}$ ratio is $\leq 0.60$.

9. The mixed oxide active material of claim 1, wherein the $V_B$ to $V_{BA}$ ratio is $\leq 0.50$.

10. The mixed oxide active material of claim 1, wherein the $V_B$ to $V_{BA}$ ratio is $\leq 0.45$.

11. The mixed oxide active material of claim 1, wherein the $V_B$ to $V_{BA}$ ratio is from 0.40 to 0.60.

12. The mixed oxide active material of claim 1, wherein the $A_B$ to $V_B$ ratio is $\geq 26$ cm$^{-1}$ and the $V_B$ to $V_{BA}$ ratio is $\leq 0.45$.

13. The mixed oxide active material of claim 1, wherein the geometric base body is a shape selected from the group consisting of a cylinder, a pyramid, a cone, a cube, a right parallelepiped, a prism, a sphere, a truncated cone, and a truncated pyramid.

14. The mixed oxide active material of claim 1, wherein the geometric body is in the shape of a ring.

15. The mixed oxide active material of claim 1, wherein the geometric body has an annular geometry having a diameter of from 5.5 mm to 7 mm, a height of 3 mm, and an internal diameter of from 3.5 to 5 mm.

* * * * *